United States Patent [19]
Ruffa

[11] Patent Number: 5,717,657
[45] Date of Patent: Feb. 10, 1998

[54] ACOUSTICAL CAVITATION SUPPRESSOR FOR FLOW FIELDS

[75] Inventor: Anthony A. Ruffa, Hope Valley, R.I.

[73] Assignee: The United States of America as represented by the Secretary of the Navy, Washington, D.C.

[21] Appl. No.: 682,880

[22] Filed: Jun. 24, 1996

[51] Int. Cl.$^6$ .......................... H04B 11/00; H04B 15/00
[52] U.S. Cl. .................................. 367/131; 367/901
[58] Field of Search ................................ 367/131, 901

[56] References Cited

U.S. PATENT DOCUMENTS

| | | | |
|---|---|---|---|
| H1357 | 9/1994 | Ng et al. | 367/901 |
| 3,757,288 | 9/1973 | Morin | 367/901 |
| 3,910,216 | 10/1975 | Shultz | 367/141 |
| 4,192,246 | 3/1980 | Hodges et al. | 114/23 |
| 4,429,652 | 2/1984 | Stol | 114/20 R |

*Primary Examiner*—Ian J. Lobo
*Attorney, Agent, or Firm*—Michael J. McGowan; Prithvi C. Lall; Michael F. Oglo

[57] ABSTRACT

A cavitation suppressor using acoustic energy to suppress flow field cavitation is provided. The suppressor system has a plurality of pressure transducers located along the outer surface of a sonar dome. These transducers are powered through a controller which receives flow data, that is, pressure fluctuations in the flow field and in response operates acoustic arrays located aft of the pressure transducers. The controller provides a sonic impulse having frequency and pulse duration selectant to reduce cavitation in the flow field around the sonar dome.

5 Claims, 5 Drawing Sheets

ACOUSTICAL CAVITATION SUPPRESSOR FOR FLOW FIELDS

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

(1) Field of the Invention

The invention relates to the technology field of flow cavitation and in particular to devices using acoustic pressure to suppress cavitation.

(2) Description of the Prior Art

Cavitation of hydrodynamic surfaces is a result of pressure variations in a fluid flow field wherein the vapor pressure of the fluid is reached typically due to propeller or hydrofoil flow. However, at sufficiently high hull speeds, cavitation can occur on certain surfaces of a hull having sufficient curvature, such as are found on sonar domes or other sensor covers. There are numerous examples of devices or methods of suppressing cavitation known in the art. Typically, the primary means of reducing cavitation is to lower the pressure differentials created in the fluid flow field, for example, by reducing the loading of a propeller. Alternately, the overall pressure of the flow field may be increased, thereby reducing cavitation, for example, in enclosed pumps. It is also well known in the art that operation of sonar devices in itself, can cause cavitation due to the negative pressures created by the generated sound field. These negative pressures cause the pressure of the water to drop below the vapor pressure, thereby allowing the water to vaporize.

The onset of cavitation typically begins with extremely small microscopic bubbles of air that are trapped in cracks or cavities of any small suspended particulate matter in the water. Additionally, free microscopic air bubbles may exist which have not gone into the solution due to impurities in the water. In the presence of a sonar impulse, these micro-bubbles act as nuclei for evolving of gasses when the water is subjected to the negative pressure portions of a sound wave. For acoustic projectors, this cavitation effectively limits the useable acoustic power which may be radiated by sonar devices. In order to increase the cavitation threshold, prior art devices have used three approaches, increasing the transmitted frequency, decreasing the pulse duration, and increasing the depth of the projector. As the duration of the negative pressure applied to the water affects the cavitation, it is possible to increase the cavitation threshold pressure so that it is greater than the negative pressure in the fluid without causing cavitation provided that the pressure interval is sufficiently short. Methods for doing this are described in R. J. Urick, "Principles of Underwater Sound", 1975, page 72.

Added to the problem of acoustically-induced cavitation, where the acoustic sensor is moving through the water, the fluid flow around the sonar dome can also cause flow-induced cavitation. The combination of acoustic and flow-induced cavitation presents a significant limitation on the operation of high power sonars. What is needed is a means to cause an acoustic pressure wave to suppress flow-induced cavitation.

SUMMARY OF THE INVENTION

Accordingly, it is an object of the invention to provide a means for sensing cavitation along a flow surface.

It is a further object of the invention to provide a means for suppressing flow-induced cavitation.

It is yet another object of the invention to provide an acoustic suppressor having a means of generating high frequency, high amplitude acoustic waves.

In accordance with these objects, the invention is an acoustic suppressor for suppressing induced flow cavitation comprising a plurality of pressure sensors attached to a flow surface and high-power active acoustic arrays mounted on the inner wall of the flow surface. The sensors are connected to a power supply and controller which are also connected to the active arrays. Upon detection of cavitation, the controller causes the active array to generate high frequency (e.g., 300–500 kHz) and high amplitude acoustic waves. The repetition rate of the acoustic impulses cause an alternating positive pressure and negative pressure pattern having a duration interval (of the negative pressure) sufficiently short that cavitation does not occur as shown in the experimental results documented by Urick supra. The active array is made up of plane piston transducers mounted on rigid baffles. The baffles have a diameter extending for several wavelengths (the acoustic wavelength at 500 KHz is 0.1 inch). The preferred embodiment is designed to suppress flow-induced cavitation around a sonar dome, however, the invention is adaptable for suppression of cavitation in any flow environment including propellers and hydraulic turbines.

BRIEF DESCRIPTION OF THE DRAWINGS

The foregoing and other objects of the present invention will be more fully understood from the following detailed description and reference to the appended drawings wherein.

DESCRIPTION OF THE PREFERRED EMBODIMENTS

Figure 1:
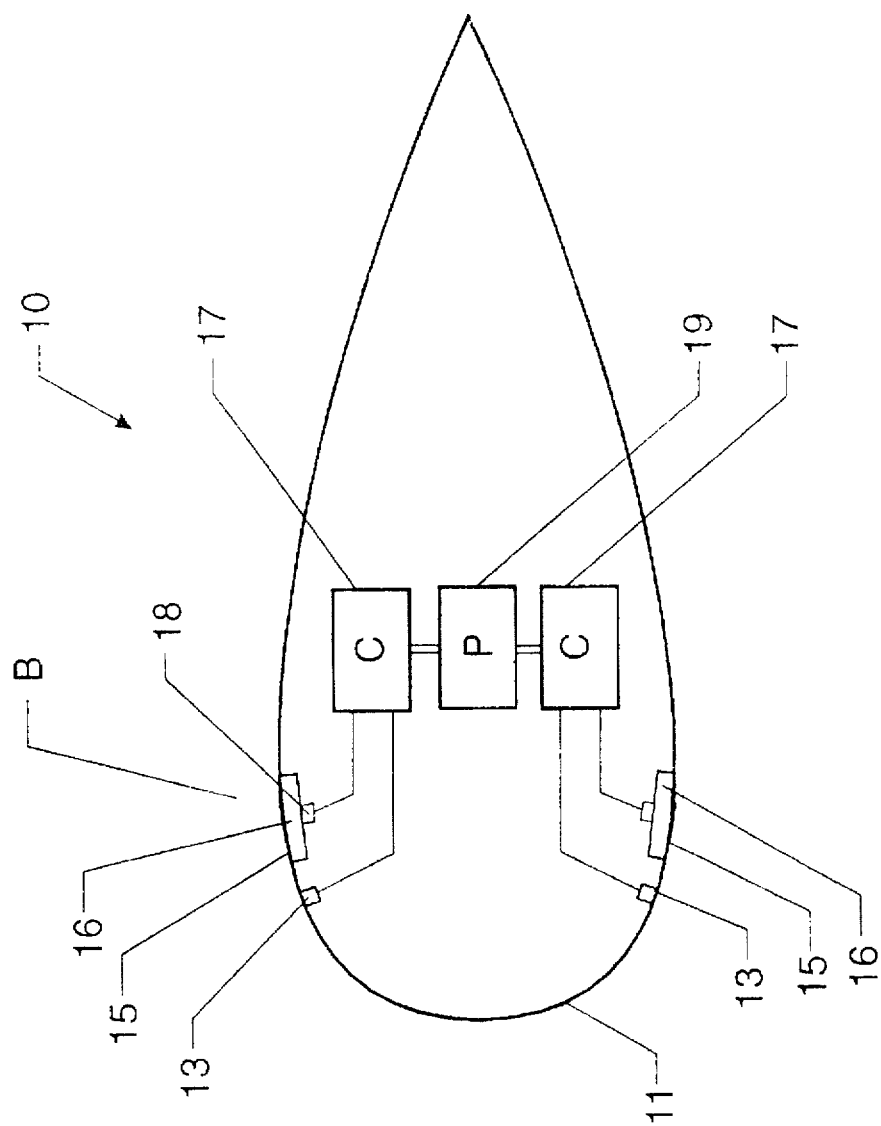
FIG. 1 is a schematic showing the components of the sonar/acoustic suppressor housing.

Referring now to FIG. 1, a schematic view of a sonar dome 11 is shown with the cavitation suppressor system, designated generally by the reference numeral 10, located within a sonar housing. The sonar dome 11 has a series of passive transducers 13 affixed to the external surface. Downstream, aft of the passive transducers 13, active transducers 15 are located. The passive transducers 13 and the active transducers 15 are connected to controllers 17 which are in turn connected to the power supply 19. Typically, a standard sonar array, not shown, is housed in the sonar dome 11. In the preferred embodiment, the passive transducers 13 are fabricated using piezoelectric material selected to conform to the required frequency response. Alternatively, the passive transducers may be fabricated using a piezoelectric polymer film depending on the particular application of the suppressor. In operation, the acoustic suppressor system detects high-level broadband noise characteristic of cavitation using the passive transducers 13. The flow field pressure frequencies and amplitudes are monitored by the controller 17 which then activates an acoustic signal through active transducers 15 once a pre-determined threshold is reached.

Typically a fairing surrounding a sonar array and a sonar dome 11 are made of a compliant rubber composite. Although the sonar dome in the preferred embodiment is made of this composite material, that is not critical to this invention. High-frequency (e.g., 300–500 kHz), high-power active arrays 15 are mounted to the inner wall of the surface at point B. The array elements consist of plane piston transducers mounted on a rigid baffle plate 16 which has a diameter extending several wavelengths from the edge of the piston 18 (the acoustic wavelength at 500 kHz is 0.1 inch). The location of the array 15 corresponds to the low-pressure region on the sonar dome, which is determined experimentally or by modeling the location of the expected cavitation. The purpose of the arrays 15 is to generate high-amplitude, high-frequency acoustic waves to increase the cavitation threshold. Experimental results documented by Urick indicate that the cavitation threshold at 550 kHz can be as high as 150 to 380 atmospheres, although other references (R. T. Beyer, "Nonlinear Acoustics", Naval Ship Systems Command, 1974) indicate that the cavitation threshold may be lower. Other experimental evidence presented by Strasberg (Acoust. Soc. Am. 31, p 163, 1959; FIG. 8) shows that as the static pressure is decreased the peak sound pressure decreases less rapidly even down to a static pressure of one-third atmosphere.

Figure 2:
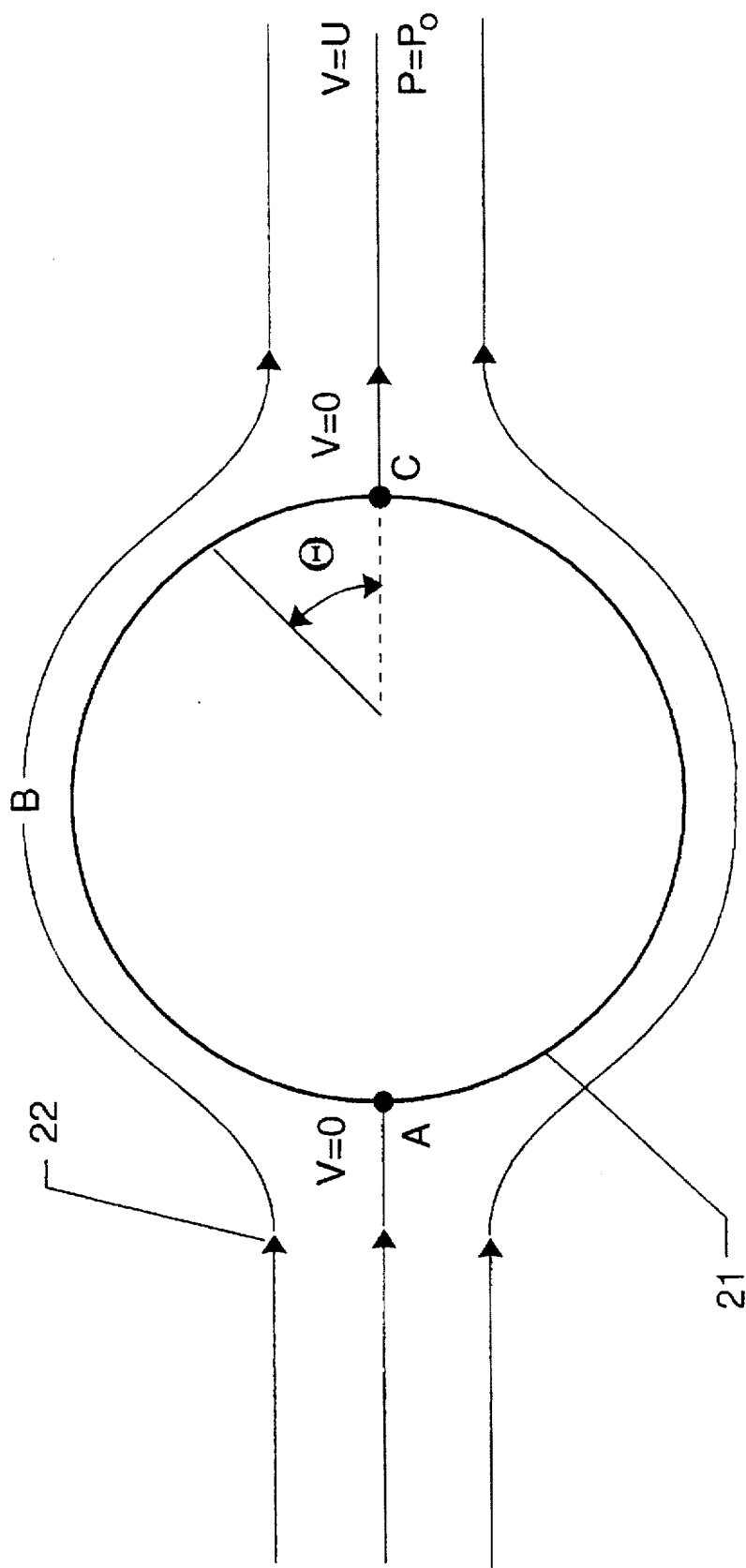
FIG. 2 is a schematic showing a simple model of the sonar/acoustic suppressor housing.

A simple model of the flow around a sonar dome is shown in FIG. 2. In this figure, flow around a cylindrical buff body 21 is shown. The freestream velocity V is defined as U and the freestream pressure is defined as $P_o$. Point A on the buff body 21 is the stagnation point where the approaching flow divides and flows over the upper and lower surfaces. As the flow, shown by arrow 22 moves around the buff body 21 and passes point B, the velocity increases as compared to freestream velocity. The pressure relationship may be determined by considering a cylinder moving through the water. By choosing a coordinate frame for which the cylinder shown in FIG. 2 is at rest, it can be shown that the velocity at point "A" is zero. Assuming inviscid flow, one of the streamlines (the curves tangent to the flow) coincides with the outer surface of the cylinder. The velocity along this streamline can be shown to be V=2Usin θ Bernoulli's equation shows that the pressure on the surface is $$P = P_0 - \frac{1}{2} \rho U^2 \quad (1)$$

The velocity that would cause the pressure to fall below the vapor pressure for water (which would cause cavitation) is $$V = \sqrt{\frac{2P_0}{\rho(4\sin^2\theta - 1)}} \quad (2)$$

As an example, a velocity of 8.21 m/s or 16 kt will lead to cavitation at point B. FIG. 2 depicts an idealized model of flow over a cylinder. It does not take into account the occurrence of flow separation at the aft end of the cylinder. Flow separation describes the departure of the streamlines from the outer surface of the cylinder. The velocity at point C would no longer be zero, which would decrease the pressure at that point.

Figure 3:
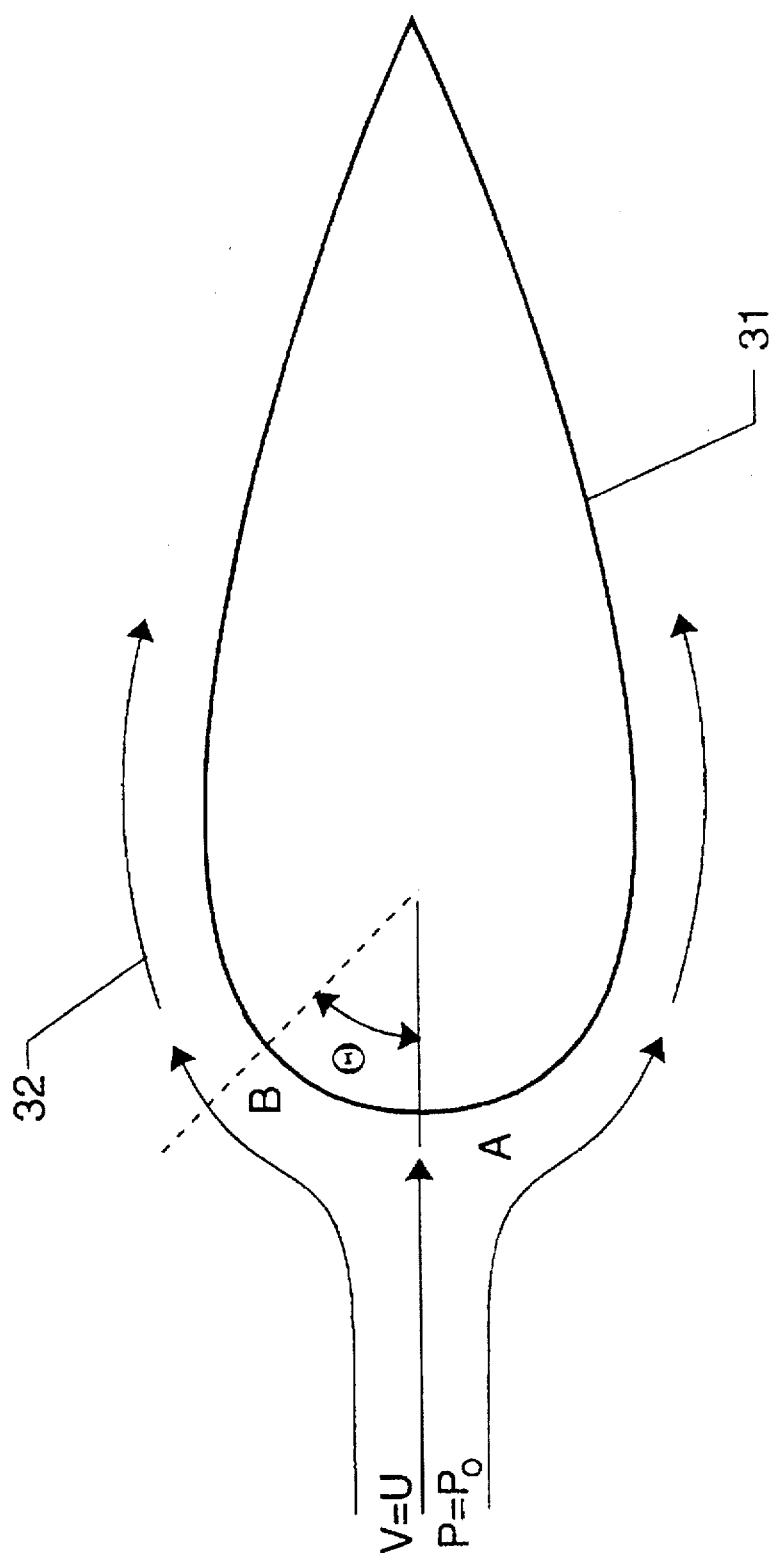
FIG. 3 is a schematic showing the flow field around the sonar/acoustic suppressor housing.

FIG. 3 shows a plan view form of a faired buff body. The fairing 31 is specifically designed to preclude flow separation. Therefore, one of the streamlines 32 will be as shown in FIG. 3, i.e., it will trace out a curve slightly displaced from the outer surface. This is due to the no-slip condition which is required of real fluids. Since the body is not moving in the chosen reference frame, the velocity on the surface must be zero. The velocity a small distance from the surface (outside the boundary layer) will be close to that predicted by inviscid flow. The velocity at point A will be close to zero and at point B will be substantially higher than the freestream velocity, causing cavitation at point B for a sufficiently high free-stream velocity. Any surface roughness or excessive compliance of the surface can cause flow oscillations which can lower the velocity causing cavitation.

In general, the amplitude of negative pressure (tension) applied to the liquid is very high if its duration is sufficiently small. The pressure amplitude $P_A$ necessary to suppress flow-induced cavitation must satisfy the following formulas:

$$P_A - \frac{1}{2} \rho V^2 > sf \quad (3)$$

$$P_A + \frac{1}{2} \rho V^2 + sf < P_c \quad (4)$$

Here sf is a safety factor and $P_c$ is the lowest cavitation threshold observed for the particular depth and frequency. As an example, if V=16 kt and f=550 kHz, $P_A$ should be greater than 1 atm plus a safety factor and less than the cavitation threshold minus a safety factor. Note that $P_A$ is the pressure exterior to the wall 5. Both the attenuation and the impedance mismatch between the wall and the water must be accounted for in computing the pressure amplitude of the array to arrive at $P_A$. In most cases, the difference in pressure across the wall will not be large.

The velocities specified in the above equations are based on ideal flow around a cylinder and are therefore conservative. The arrays need not be turned on until cavitation actually occurs (i.e., when self-noise is degraded).

Figure 4:
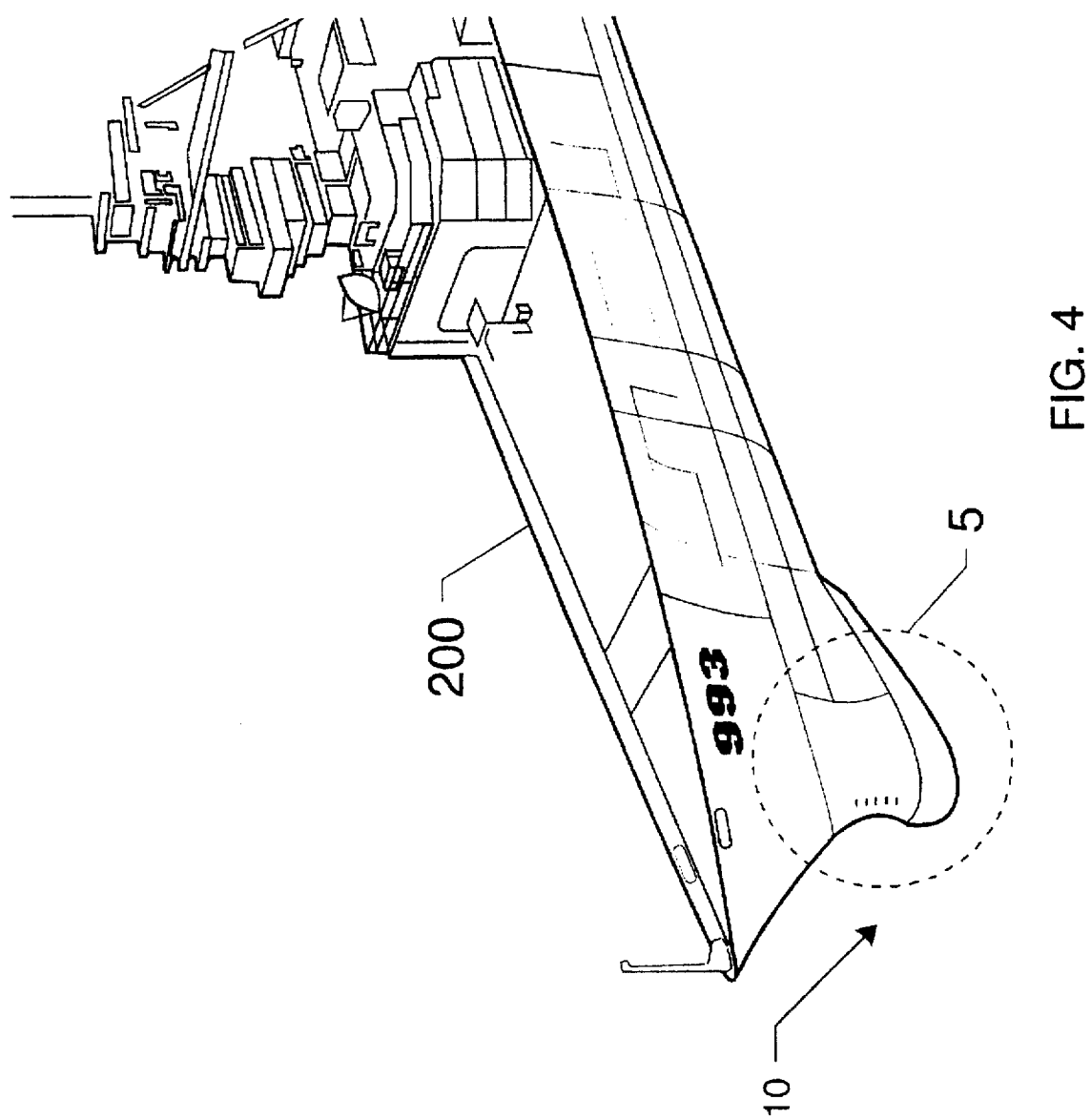
FIG. 4 is a partial view of a ship showing the location of a ship-mounted sonar array having a co-located acoustic suppressor.

Referring now to FIG. 4, a representative installation is shown on the hull of ship 200. The cavitation suppressor installation is located in the forward hull section enclosed by dotted circle 5. A more detailed representation is shown in FIG. 5 which is an enlarged view of dotted circle 5.

Figure 5:
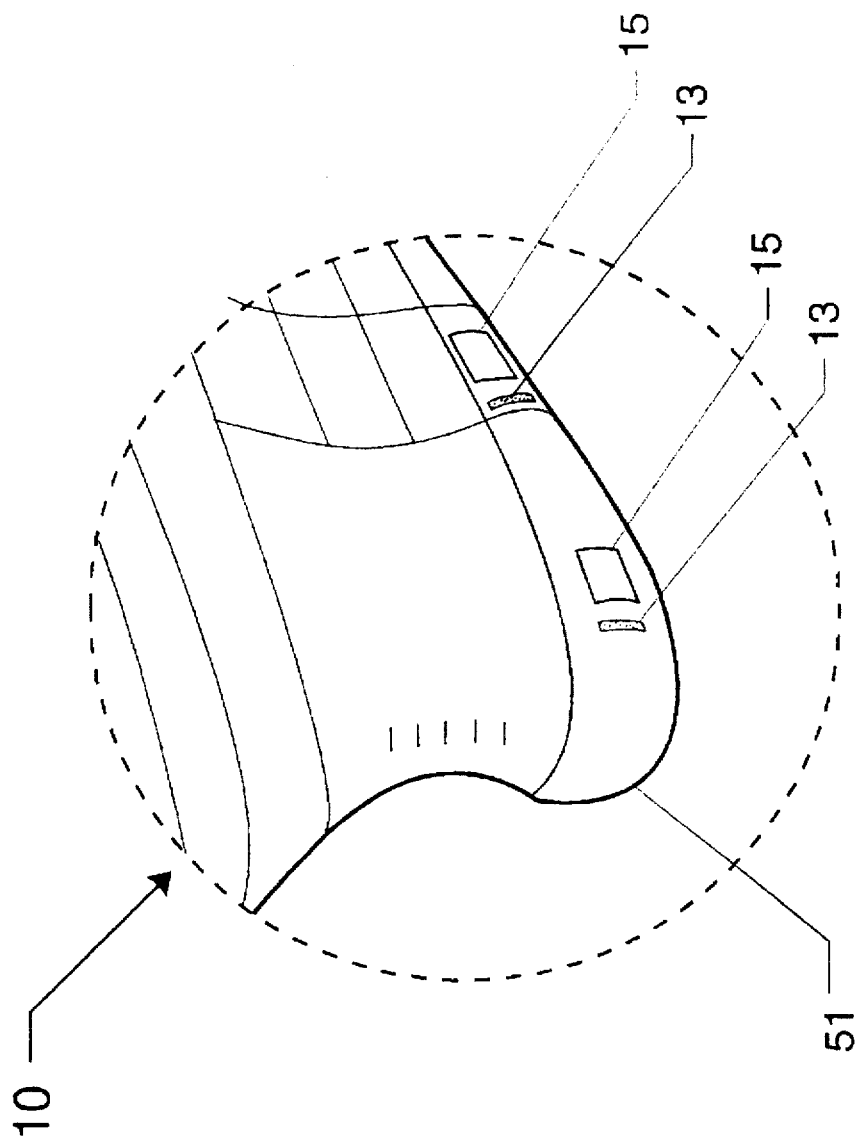
FIG. 5 is an enlarged view of the sensor and acoustic suppressor housing.

Referring now to FIG. 5, an example of a sonar dome 51 for forward-looking sonar arrays is shown. The passive transducers 13 are located slightly forward of the active transducers 15. Operation of the cavitation suppressor, is as previously described.

The features and advantages of the invention are numerous. The cavitation suppressor allows higher operating speeds for the ship 200 while reducing flow noise, reducing cavitation and allowing active control of flow field around the sonar dome. This invention is an apparatus for suppressing cavitation due to flow over a buff body. Although it is specifically directed toward suppressing cavitation due to flow over sonar domes, it can be used to suppress cavitation due to flow over any faired or unfaired body. It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. An acoustic suppressor for suppressing cavitation in a flow field comprising:

a sonar dome having upstream and downstream surfaces adapted for operation in a flow field;

means for detecting flow field pressure fluctuations, said means attached to the upstream surfaces of said sonar dome;

a plurality of controllers located within said sonar dome and electrically connected to said means for detecting;

a plurality of high energy active transducers attached to a rigid baffle plate having a diameter of several wavelengths of the cavitation sound frequency and located on the sonar dome surfaces downstream from said means of detecting, said active transducers being electrically connected to said plurality of controllers; and a power supply located within said sonar dome and electrically connected to said plurality of controllers.

2. An acoustic suppressor for suppressing cavitation in a flow field as in claim 1 wherein said means for detecting flow field pressure fluctuations comprise passive transducers.

3. An acoustic suppressor for suppressing cavitation in a flow field as in claim 2 wherein said passive transducers are fabricated using piezoelectric material having a frequency response suitable for detecting amplitude and frequency of the flow field.

4. An acoustic suppressor for suppressing cavitation in a flow field as in claim 2 wherein said passive transducers are fabricated using a piezoelectric polymer film material having a frequency response suitable for detecting amplitude and frequency of the flow field.

5. An acoustic suppressor for suppressing cavitation in a flow field comprising:

a sonar dome having upstream and downstream surfaces adapted for operation in a flow field;

a plurality of passive transducers attached to the upstream surfaces of said sonar dome;

a high power, active plane piston sonar array having rigid baffles attached thereto, said array mounted within said sonar dome on the downstream surfaces;

a plurality of controllers located within said sonar dome and electrically connected to and receiving signals from said massive transducers and electrically connected to and activating said high power, active sonar array; and a power supply located within said sonar dome and electrically connected to said plurality of controllers.

* * * * *